US006920399B2

United States Patent
Priev et al.

(10) Patent No.: US 6,920,399 B2
(45) Date of Patent: Jul. 19, 2005

(54) METHOD AND APPARATUS FOR DETERMINING THE COMPOSITION OF FLUIDS

(75) Inventors: Aba Priev, Jerusalem (IL); Viktor Ponomarev, Rostov-Na-Donu (RU); Armen Sarvazyan, Lambertville, NJ (US)

(73) Assignee: Nanoalert (Israel) Ltd., Tel Aviv (IL)

( * ) Notice: Subject to any disclaimer, the term of this patent is extended or adjusted under 35 U.S.C. 154(b) by 104 days.

(21) Appl. No.: 10/332,473

(22) PCT Filed: Jul. 10, 2001

(86) PCT No.: PCT/IL01/00634

§ 371 (c)(1),
(2), (4) Date: Jan. 9, 2003

(87) PCT Pub. No.: WO02/04916

PCT Pub. Date: Jan. 17, 2002

(65) Prior Publication Data

US 2003/0236635 A1 Dec. 25, 2003

Related U.S. Application Data

(60) Provisional application No. 60/217,092, filed on Jul. 10, 2000.

(51) Int. Cl.[7] ........................... G01N 31/00; G06F 19/00
(52) U.S. Cl. ........................................................ 702/23
(58) Field of Search ........................ 702/22, 23, 50, 702/54, 108, 127; 73/64.41, 64.42, 64.53, 61.45, 61.44, 61.79

(56) References Cited

U.S. PATENT DOCUMENTS

| | | | | |
|---|---|---|---|---|
| 4,145,450 A | * | 3/1979 | Winder et al. | 426/231 |
| 4,520,654 A | * | 6/1985 | Terhune | 73/24.01 |
| 4,566,312 A | * | 1/1986 | Collins et al. | 73/32 A |
| 5,298,141 A | * | 3/1994 | Irie et al. | 204/473 |
| 5,473,934 A | * | 12/1995 | Cobb | 73/61.49 |
| 5,533,402 A | * | 7/1996 | Sarvazyan et al. | 73/645 |
| 5,804,698 A | * | 9/1998 | Belonenko et al. | 73/1.83 |
| 6,114,176 A | * | 9/2000 | Edgson et al. | 436/108 |
| 6,244,101 B1 | * | 6/2001 | Autrey et al. | 73/61.45 |
| 6,260,408 B1 | * | 7/2001 | Vig et al. | 73/64.53 |
| 6,339,954 B1 | * | 1/2002 | Naganawa et al. | 73/61.79 |
| 6,350,426 B1 | * | 2/2002 | Sota et al. | 423/485 |
| 6,393,895 B1 | * | 5/2002 | Matsiev et al. | 73/24.06 |
| 6,511,851 B1 | * | 1/2003 | Payne et al. | 436/151 |
| 6,542,828 B2 | * | 4/2003 | MacDonald et al. | 702/25 |

\* cited by examiner

*Primary Examiner*—Bryan Bui
*Assistant Examiner*—Demetrius Pretlow
(74) *Attorney, Agent, or Firm*—Mark M. Friedman (57) ABSTRACT

A method and apparatus for analyzing a fluid to obtain the concentrations of N of its components, N being at least three. The method comprises the steps of bringing a sample of the fluid to a plurality of successive temperatures, measuring a combined total of at least N acoustical and electrical parameters of the sample at each temperature, and determining simultaneously from the measured acoustical and electrical parameters, using a system of N linear equations, the concentrations of the N components. The apparatus combines acoustic and electrical measuring elements in one unit.

20 Claims, 7 Drawing Sheets

METHOD AND APPARATUS FOR DETERMINING THE COMPOSITION OF FLUIDS

This application claims the benefit of Provisional Application Ser. No. 60/217,092, filed Jul. 10, 2000.

FIELD AND BACKGROUND OF THE INVENTION

The present invention relates to a method and apparatus for determining the content of fluid components, in particular of milk components, based on the generation of acoustical and electrical fields and the measurement of acoustical and electrical characteristics of the sample. More particularly the present invention can be used to determine the content of fat, protein, lactose, mineral salts and water and optionally additional components of milk, by the determination of the acoustical and electrical parameters of a milk sample at different temperatures.

There are many applications where it is desirable to determine various characteristics of a fluid, such as the concentration of material in a solution, suspension or emulsion. An example of such emulsion is milk. Milk contains globules of butterfat (2–6%), as well as 2–6% proteins (mostly casein), 4–5% milk sugar (lactose), and 0.5–1% mineral salts dispersed in an aqueous solution. The proteins, lactose and mineral salts, taken together, comprise the solid-not-fat (SNF) component. Water constitutes 80–90% of the whole milk [Bhatti, S. S. et al. Acustica, Vol. 62, p. 96–99, 1986]. The determination of the chemical components in milk and milk products is of considerable importance in the dairy industry, since the amount of such components, particularly the butterfat and protein contents thereof, is the usual basis for determining the products' price, food value and compliance with US state and federal laws and regulations.

Various attempts have been made to determine the content of milk components using different physical methods. U.S. Pat. No. 5,033,852 discloses an optical measuring device for measuring the fat content of milk. The optical measurement device comprises a light source, an optical condenser, a glass test tube provided for holding a set amount of the milk to be tested, a tubular housing for the milk test tube; a lens and a photosensitive element, and a digital display. The milk fat content is obtained by automatically measuring, using the photosensitive element, the diffusion depth of the light projected on a milk sample. The device provides quick, accurate and reliable measurement results. However the disclosed method is limited in its application to determining the fat content, and other milk component cannot be analyzed.

U.S. Pat. No. 5,983,709 describes a device and method for measuring, monitoring, and controlling the fat and protein (micellar associated protein) content of a milk sample. The invention is especially adaptable for the standardization of milk for cheese production. The device consists of a sampling inlet feeding a milk sample into a diluter. The diluter has the ability to select an appropriate diluent for dilution that renders the milk sample analyzable by a spectrophotometer. For fat determination, the milk sample is diluted with a detergent-chelating agent that breaks up micellar protein. Light absorbance readings on the spectrophotometer of chelator-detergent diluted milk samples are concentration-dependent only on the fat content. Dilution of the milk sample with water gives absorbance readings that are dependent on the concentration of fat plus micelle-associated proteins. The micelle-associated protein concentration can then be obtained by subtracting the fat concentration from the total. The method described involves many steps, protein and fat determination are carried out in different samples and the protein determination is indirect since it is based on the subtraction of the fat concentration of the sample from the fat-plus-protein concentration. Since the fat and fat-plus-protein contents are measured by light absorbance, only fat and micelle-associated proteins such as caseins can be determined, while other milk components such as salt and lactose cannot be analyzed.

U.S. Pat. No. 4,566,312 describes apparatus and processes for automatic determinations of fat contents of foods, such as diary products, e.g. milk, wherein automatic density and solids content determining apparatus are employed, together with a computer, to determine the fat content of food being tested. The density determining apparatus is preferably one that is electromagnetically excited to vibrate at its natural resonant frequency, so that the mass of the sample may be determined from the change in such frequency, in comparison with a control. The means for measuring the solids content include electromagnetic radiation (microwave energy), which is employed to drive off the volatile material (usually mostly water) in the sample, which is automatically weighed before and after such volatilization. The fat content is calculated from the data on the density and the solids content. By means of this invention the fat contents of diary products, as well as contents of certain comparable components of other materials can be rapidly and accurately determined from small samples of such materials, thereby facilitating rapid evaluations, production controls and standardization of such materials leading to an important saving of time and money. However the apparatus described is applicable only for fat determination, while other milk components cannot be analyzed.

U.S. Pat. No. 4,447,725 describes an improved electro-optical apparatus for measurement of fat, protein, lactose and solids in milk. The invention also discloses an improved method and apparatus for quantitatively measuring fat concentration in fat emulsions such as synthetic and natural dairy products, including specifically milk, which minimizes errors and inconsistencies due to variations in fat molecular weight or degree of lipolysis. The method is based on irradiation of a milk sample with energy in the infrared spectrum at a wavelength characteristic of different linkages, groups and bonds. The apparatus described cannot be used to measure milk samples (e.g. taken from a cow) on-line, and requires transferring samples to a laboratory, which lengthens the time of analysis.

It is widely recognized that there is a lack of suitable sensors for providing information about the physicochemical properties of foods, especially for the continuous monitoring of foods (milk, wine, juices and others) during processing. One of the major problems in developing analytical techniques for use in the food industry is the diversity and complexity (both compositional and structural) of liquid food products. Many traditional "wet-chemistry" techniques have limited application because they are destructive, time consuming, and labor intense. Consequently there has been a drive to develop new technologies, or to apply techniques currently used in other areas, for analysis of liquid food products.

Over the last decade there has been increasing interest in the use of ultrasound for characterizing food materials. In this technique, a high-frequency sound wave is propagated through the material being tested. Information about the properties of a material is then obtained by measuring the type and degree of interaction between the sound wave and the material. Ultrasound has major advantages over many other analytical methods because it is nondestructive, rapid, precise, relatively inexpensive, and can be applied to concentrated and optically opaque samples [McClements, D. J., Critical Reviews in Food Science and Nutrition, Vol. 37, p. 1–46, 1997].

As known in the art, e.g. as exemplified by the teachings of U.S. Pat. No. 3,040,562, the ultrasound velocity propagation in whole milk varies with the amount of fat present in the milk and with the sample temperature. U.S. Pat. No. 4,145,450 discloses a method and apparatus for controlling the butterfat content of a stream of milk on a continuous basis. The innovation of the method disclosed is the determination of sound velocity at two different temperatures, preferably 45° C. and 65° C., and the application of an equation system from which high concentrations of milk components can be determined.

U.S. Pat. No. 4,145,450 shows that the ultrasound velocity, U, in the milk is directly correlated with the percentage of butterfat (%F) and the percentage of solids-not-fat (%SNF) in the milk, with the relationship between U, %F and %SNF dependent upon the particular temperature of the milk. Consequently, by measuring ultrasound velocity at two temperatures, e.g. at 45° C. and 65° C., it is possible to evaluate the fat content in the milk. Thus, the following simultaneous linear equations could be solved:

$$U^{45} = K_1(\%F) + K_2(\%SNF) + K_3$$

$$U^{65} = K_4(\%F) + K_5(\%SNF) + K_6$$

where $U^{45}$ and $U^{65}$ are the ultrasound velocity at respectively 45° C. and 65° C., and $K_1$–$K_6$ are parameters determined empirically by correlation with a separate analysis performed by known chemical methods, $K_1$–$K_6$ hold substantially constant for butterfat levels ranging between 0 and 20%. For a wider range of fat content, second order equations are needed. The method described in U.S. Pat. No. 4,145,450 is limited in its application for analyzing the butterfat and solid-not-fat content of milk, while constituents of the solid-not-fat itself (i.e. protein, lactose and salts) and other milk components cannot be determined.

Since the quality and price of the milk product is determined according to the percent of fat, protein and somatic cells, previous methods that determine only %F and %SNF are not adequate.

There is thus a widely recognized need for, and it would be highly advantageous to have, an apparatus and method for the simultaneous, on-line determination, of the content of at least three components of a fluid, in particular milk, rapidly and accurately, using small samples of the fluid.

SUMMARY OF THE INVENTION

The present invention discloses an innovative method and apparatus for determining the content of fluid components, particularly milk or other liquid food products, based on the generation of acoustical and electrical fields in the sample.

Specifically, the present invention can be used to determine the content of fat, protein, sugar, salt, somatic cells, water, and optionally additional components by the determination of the acoustical and electrical parameters of the fluid sample at different temperatures.

More specifically, the present invention uses the combined measurement of acoustical parameters and their temperature derivatives (slopes) together with electrical conductivity of a fluid, for example milk, to obtain N independent parameters that can be used in a set of N equations, N being at least three, to evaluate at least three fluid component concentrations, which include, in the case of milk, SNF components. The combined use of acoustic and electrical measurements that yield the compositions of at least three fluid components is novel and non-obvious, and a key feature of the present invention.

According to the present invention, there is provided a method of analyzing a fluid, comprising the steps of: a. bringing a sample of the fluid to a plurality of successive temperatures; b. measuring N physical parameters of the sample, N being at least three, at each temperature; and c. determining simultaneously the concentrations of N components of the fluid, N being at least three, using the physical parameters, thereby obtaining a quantitative composition of the fluid.

According to the present invention, there is provided an apparatus for the simultaneous determination of the concentrations of N components of a fluid, N being at least three, comprising: a. a measuring unit including at least one acoustical and at least one electrical measurement cells; b. means for introducing a sample of the fluid into the measuring unit; c. thermostating means to bring the fluid sample to a series of temperatures; d. means for measuring acoustical and electrical parameters of the fluid sample; and e. data processing means for evaluating the concentrations of the N components from the measured acoustical and electrical parameters.

BRIEF DESCRIPTION OF THE DRAWINGS

The invention is herein described, by way of example only, with reference to the accompanying drawings, wherein.

DESCRIPTION OF THE PREFERRED EMBODIMENTS

The present invention discloses an innovative method and apparatus for determining the content of fluid components, particularly milk or other liquid food products, based on the generation of acoustical and electrical fields in the sample.

Specifically, the present invention can be used to determine the content of fat, protein, sugar, salt, somatic cells, water, and optionally additional components by the determination of the acoustical and the electrical parameters of the fluid sample at different temperatures.

More specifically, the present invention uses the combined measurement of acoustical parameters and their temperature derivatives (slopes) together with electrical conductivity of a fluid, for example milk, to obtain at least three independent parameters that can be used in a set of at least three linear equations, to evaluate at least three fluid component concentrations.

The principles and operation of the apparatus according to the present invention may be better understood with reference to the drawings and the accompanying description.

Before explaining at least one embodiment of the invention in detail, it is to be understood that the invention is not limited in its application to the details of construction and the arrangement of the components set forth in the following description, or illustrated in the drawings. The invention is capable of other embodiments, or of being practiced or carried out in various ways. Also, it is to be understood that the phraseology and terminology employed herein is for the purpose of description and should not be regarded as limiting.

Figure 1:
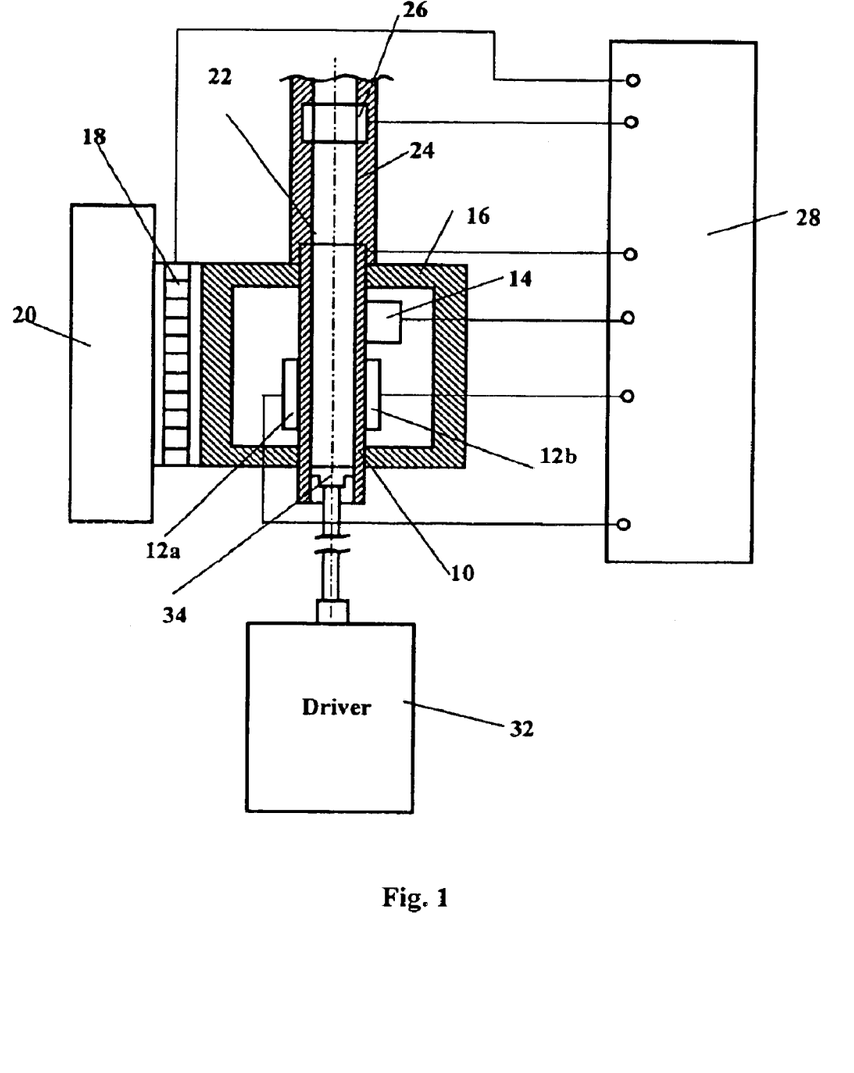
FIG. 1 illustrates a preferred embodiment of the apparatus of the present invention.

FIG. 1 illustrates a preferred embodiment of the apparatus of the present invention. The apparatus includes a measuring chamber 22 used for measurements of acoustical parameters of a fluid sample, whose main elements are an acoustical cell 10 and an electrical cell 24. Preferably, acoustical cell 10 is a cylindrical acoustical standing wave resonator, and electrical cell 24 is an electrical conductivity measurement tube with a metal ring electrode 26. A particularly advantageous embodiment of cell 10 is similar to that employed in U.S. Pat. No. 5,533,402, which is incorporated by reference for all purposes set forth herein. U.S. Pat. No. 5,533,402 discloses a method and apparatus for analyzing liquids utilizing cylindrical acoustic standing waves, generally in the ultrasonic region. The invention facilitates measurements of acoustic parameters of a fluid such as sound velocity and attenuation. A central component of the invention is the cylindrical resonator used to contain fluid and generate cylindrical standing waves therein. The resonator may be a radially polarized cylindrical piezoelectric tube having self associated electrodes, or a non-piezoelectric tube acoustically coupled to a source of oscillation.

In the present invention, tubes 10 and 24 are most preferably placed in series, forming a single tube. Cell 10 includes a piezotransducer 12 having a transmitting piezotransducer 12a and a receiving piezotransducer 12b. Cell 10 is placed in a thermostating unit that includes a thermo sensor 14 attached to tube 10, a thermal jacket 16 with a Peltier element 18, and a heat sink 20. The apparatus also includes an electronic unit 28, and a driver 32 used for moving a piston 34 inside tube 10 for delivering and removing the sample of the measured liquid (i.e. supplying the sample for both acoustical and electrical measurements).

Figure 2:
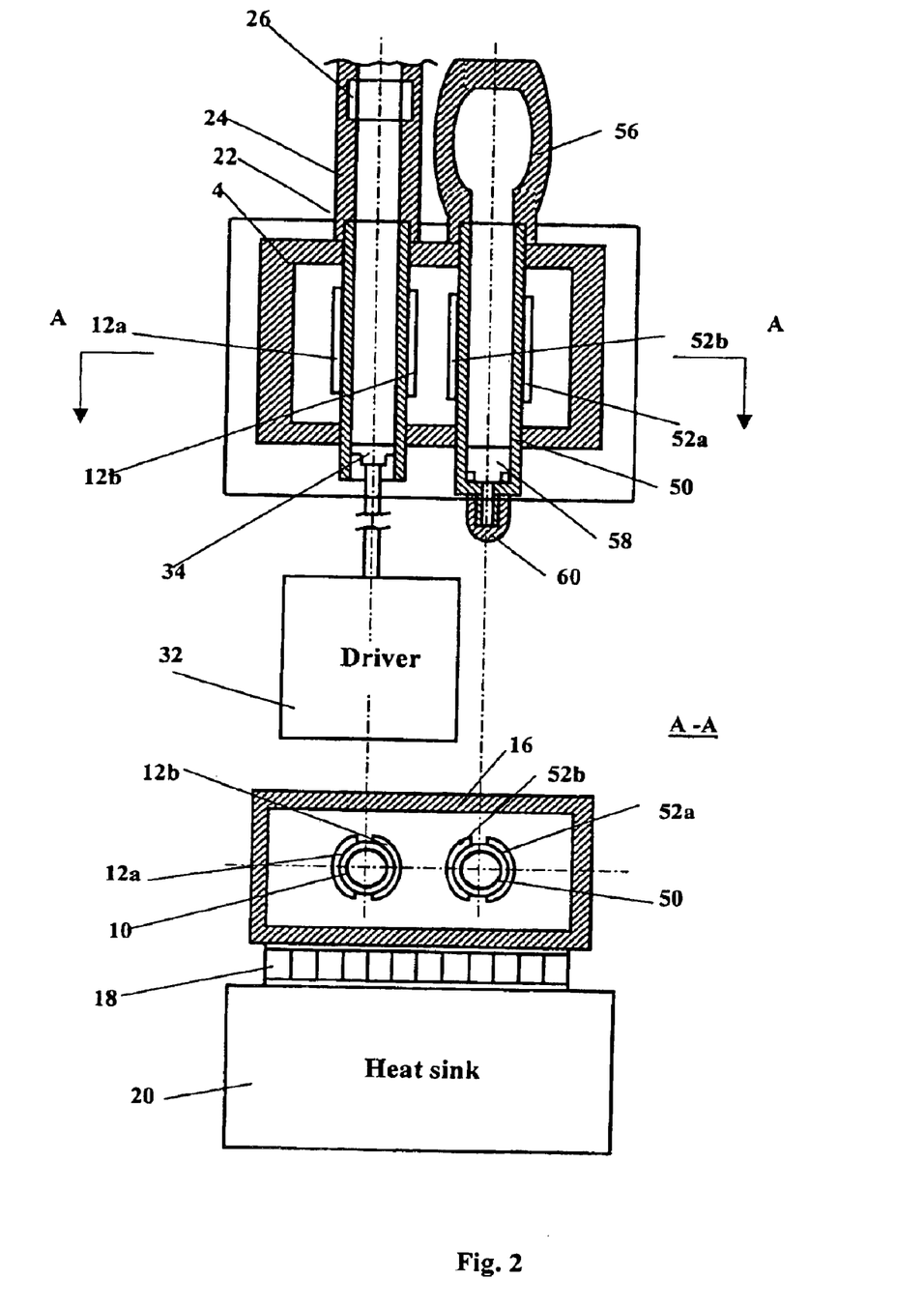
FIG. 2 illustrates another embodiment of the apparatus that uses a differential principle of measurement.

FIG. 2 shows another embodiment of the apparatus of the present invention, which includes a second acoustical cell 50 with two piezotransducers, a transmitter 52a and a receiver 52b. Tube 50 is preferably placed in thermal jacket 16 symmetrically in relation to tube 10. Tube 50 has an elastic plug 56, a stopper 58 and a hermetic sealing cap 60. Section A—A shows the apparatus in a different perspective.

Figure 3:
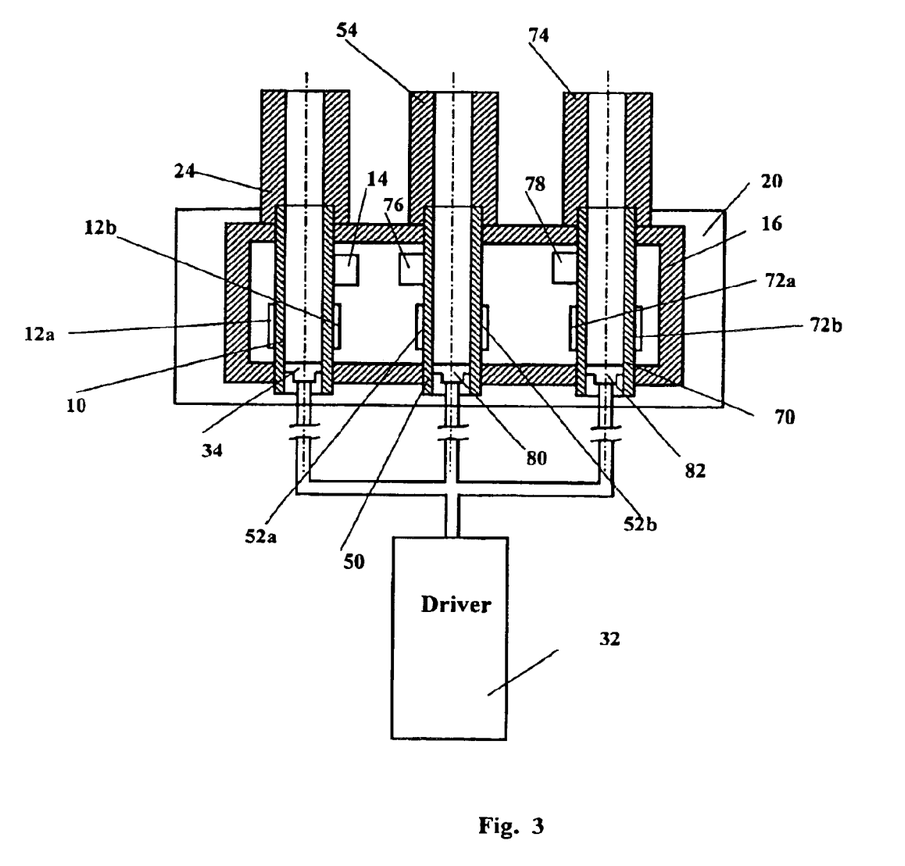
FIG. 3 illustrates an embodiment with three measuring cells connected in parallel, each cell enclosed in a separately thermostated thermal jacket.

FIG. 3 shows a yet another, multichannel embodiment of the apparatus of the present invention. In this embodiment, resonator tubes 10, 50, and a third tube 70 are located in common in thermal jacket 16 and have identical design elements, namely: piezotransducers (transducers 12a, 52a, and 72a, and receivers 12b, 52b, and 72b; tubes 10, 54, and 74; thermo sensors 14, 76 and 78; and pistons 34, 80, and 82.

Figure 4:
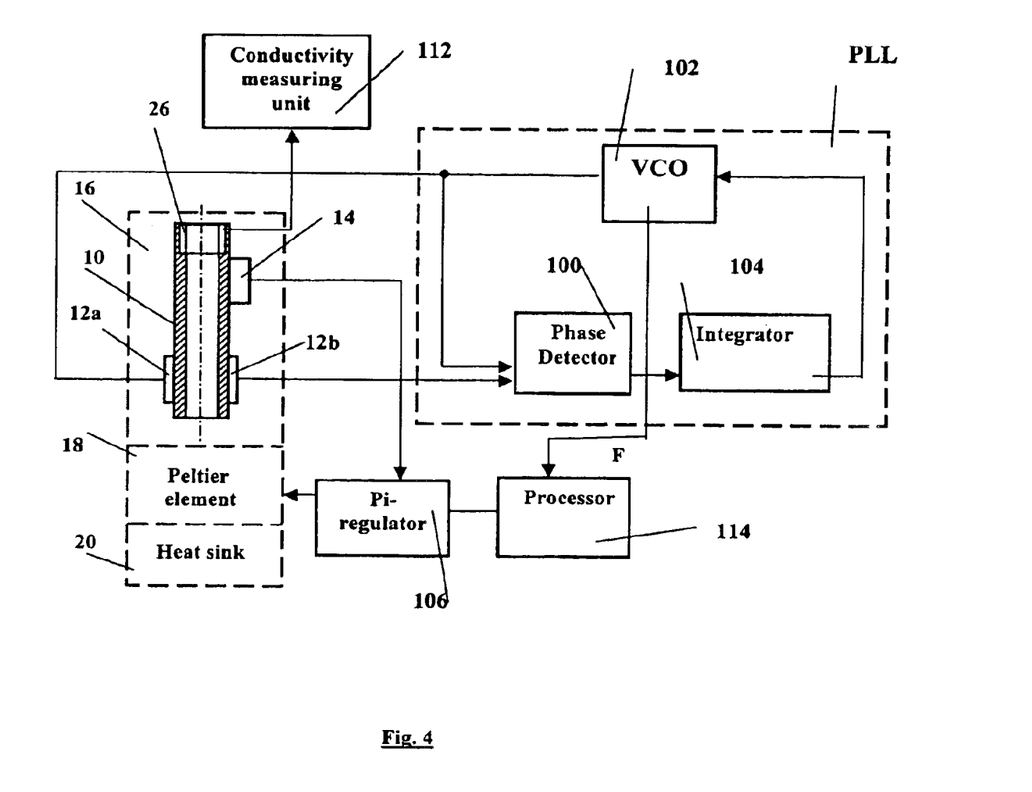
FIG. 4 shows a detailed view of an electronic unit that is used to control the apparatus.

FIG. 4 shows a detailed view of electronic unit 28, which is used to control the apparatus. Unit 23 typically includes a phase detector 100, one input of which is connected to receiver 12b, and a second input of which is connected to the output of a voltage controlled controlled oscillator (VCO) 102 and to transducer 12a. The output of phase detector 100 is connected to the input of an integrator 104, which has its output connected to the input of oscillator 102. In addition and optionally, unit 28 may include a pi-regulator 106, which has an input 108 connected with thermosensor 14, and has an output 110 connected to Peltier element 18. Unit 28 may further include a conductivity-measuring unit 112, connected to electrode 26. A processor 114, operationally connected to both the acoustic elements and the pi-regulator, is used to measure the operating frequency F of the standing wave of the acoustical resonator, and to provide temperature control.

Figure 5:
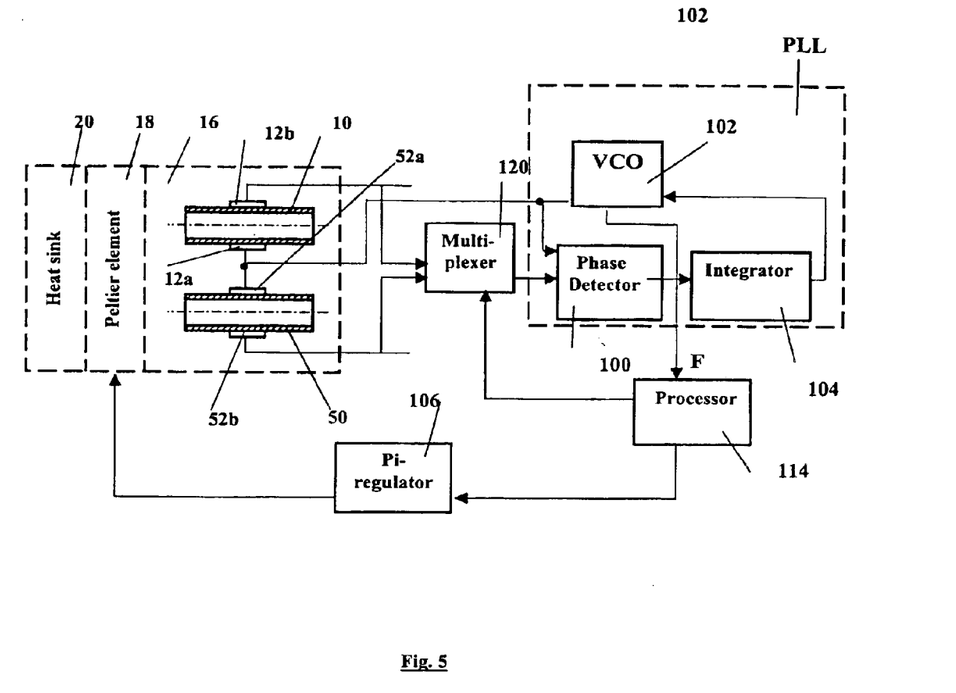
FIG. 5 shows another embodiment of the electronic unit that can be used in differential measurements.

FIG. 5 shows another embodiment of electronic unit 28 that can be used in differential measurements. In this embodiment, a multiplexer 120 is used to control switching between piezotransducers 12a,b and 52a,b.

Figure 6:
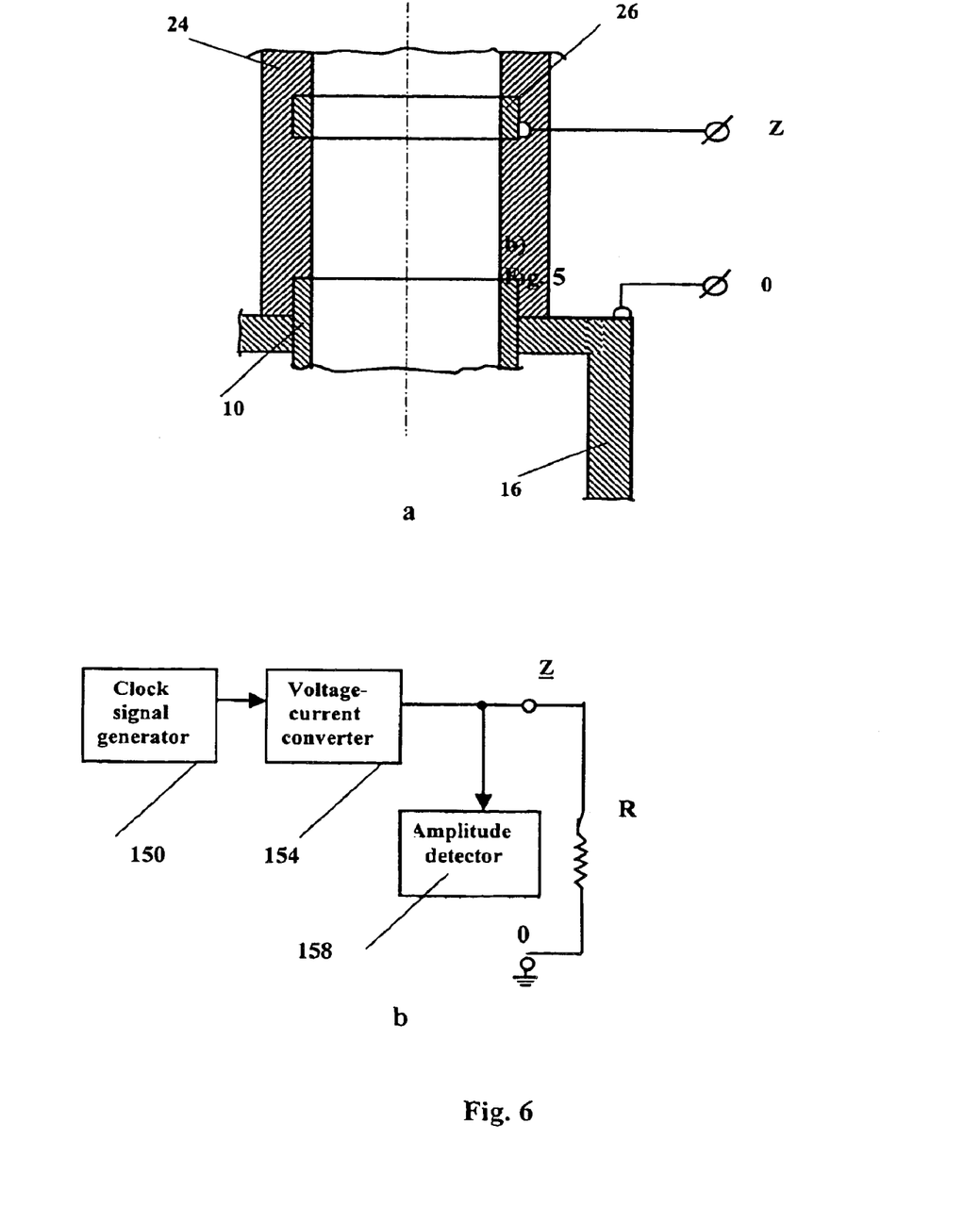
FIG. 6 shows a more detailed view of a conductivity-measuring unit.

FIG. 6 shows a more detailed view of conductivity measuring unit 112, which includes (in "b") a clock signal generator 150 that is electrically connected to an input 152 of a voltage-current converter 154. An output 156 of converter 154 is connected to electrode 26 (clamp Z in "a") and to an amplitude detector 158. The metal tube of acoustical cell 10 can serve as one electrode for the tube of electrical cell 24, whereas the second circular electrode 26 of the electrical cell can be separated from the metal tube of acoustical cell 10 by a segment of non-conductive tube 24.

Figure 7:
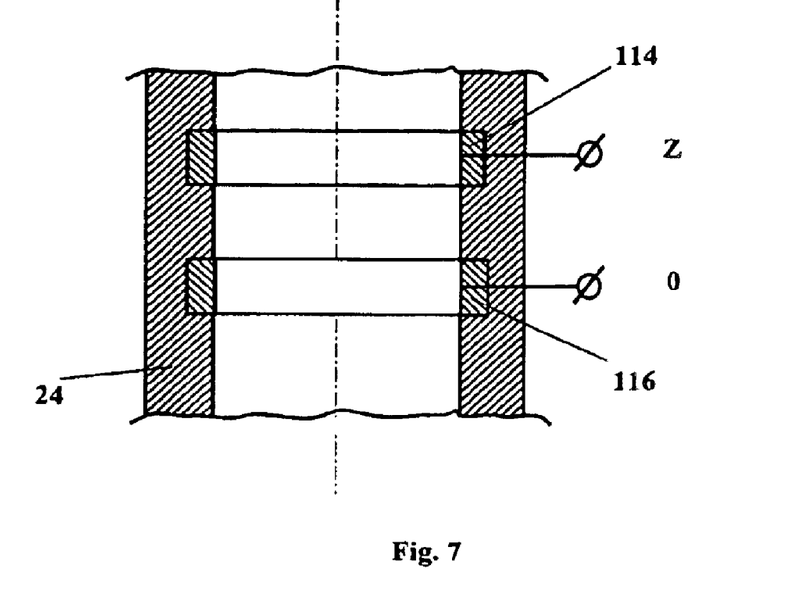
FIG. 7 shows an alternative embodiment of the conductivity measuring section having two separate electrodes incorporated in the measuring tube.

FIG. 7 shows an alternative embodiment of the conductivity-measuring unit 112 that utilizes two separate ring electrodes 114 and 116, incorporated in tube 24. Electrodes 114 and 116 are electrically connected to unit 112 by clamps Z and 0 respectively.

In a typical operating procedure, a sample of the fluid to be measured is delivered to tube 10 by moving piston 34. The desired value of the temperature of the measured fluid is reached with the help of a thermostating unit with thermosensor 14, pi-regulator 106 (FIGS. 4,5) and Peltier element 18. Ultrasonic standing waves are generated in the sample of the measured fluid with the help of the acoustical apparatus that includes acoustical resonator tube 10, piezotransducers 12a,b, phase detector 100, integrator 104 and controlled oscillator 102. The frequency F of the standing wave of the acoustic resonator is measured with the help of the processor 114. A detailed description of the procedure by which one can obtain both ultrasound velocity and ultrasound attenuation from the measured frequency F is given for example in detail in U.S. Pat. No. 5,533,402. The temperature derivatives of these two ultrasound parameters can be obtained from either a continuous measurement (many data points) of ultrasound velocity and ultrasound attenuation as the temperature is changed in a given range, for example between 20 and 30° C., or just by using two values of each parameter at the end points of the temperature range. When the measurements of all parameters involved are done continuously as the temperature is changed, the procedure is referred to as "continuous scanning". When the measurements are done after the temperature is changed from one value to another, then stabilized at that value, the temperature change is referred to as "step-wise".

As mentioned above, the geometry of the acoustic resonator is preferably cylindrical, as described in U.S. Pat. No. 5,533,402. However, it may also include parallel piezotransducers or any other arrangement of transducers capable of generating standing acoustic waves in the fluid sample. Electrical conductivity measurements in the fluid are carried out simultaneously with the acoustic measurements. Methods of measuring electrical conductivity of fluids are well known in the art. In particular, the conductivity can be measured from the active component of the complex electric impedance of a fluid sample. However, the combination of acoustic and electrical measurements in a single apparatus, wherein part of the acoustical setup may serve for the electrical conductivity measurements, is novel and nonobvious.

While the method of the present invention describes in detail the combined use of at least two acoustical parameters and at least one electrical parameter (conductivity) to obtain the concentrations of at least three fluid components, it is obvious that the use of four such combined parameters (acoustical plus electrical) can yield concentrations of four components, the use of five combined parameters can yield five component concentrations, etc. While the present invention specifies four independent acoustical parameters and one electrical parameter to yield five component concentrations, additional parameters, for example the frequency dependence of acoustical velocity, acoustical attenuation, acoustical impedance and their temperature derivatives, are fully considered to be within the scope of the present invention. Thus, in general, the present invention uses the combined (in one apparatus) measurement of N physical parameters, N being at least three and including at least two acoustical parameters and at least one electrical parameter, to obtain the concentrations of N fluid components.

The multichannel apparatus embodied in FIG. 3 provides simultaneous temperature control of several samples of the measured fluid, allowing shorter measurement times, since there is no need to spend time on changing successive temperatures and waiting for their equilibration.

Evaluation of Component Concentrations

The measurement data obtained by the apparatus described above are further processed to obtain required compositional parameters of the measured liquid sample, for example the concentration of components of milk. For example, for determining the five main components in a sample of milk (butterfat (F), protein (P), lactose (L), mineral salts (S), and water (W)) the following five simultaneous linear equations are solved by using for example a PC or similar computer system:

$$U^T = K_1(\%F) + K_2(\%P) + K_3(\%L) + K_4(\%S) + K_5(\%W)$$

$$dU/dT = K_6(\%F) + K_7(\%P) + K_8(\%L) + K_9(\%S) + K_{10}(\%W)$$

$$\alpha^T = K_{11}(\%F) + K_{12}(\%P) + K1_{13}(\%L) + K_{14}(\%S) + K_{15}(W)$$

$$d\alpha/dT = K_{16}(\%F) + K_{17}(\%P) + K_{18}(\%L) + K_{19}(\%S) + K_{20}(\%W)$$

$$C = K_{21}(\%F) + K_{22}(\%P) + K_{23}(\%L) + K_{24}(\%S) + K_{25}(\%W)$$

Where: $U^T$ is the sound velocity through the sample in the measuring cell when the sample is at a temperature T; $dU/dT$ is the sound (ultrasonic) velocity slope (derivative) as a function of temperature; $\alpha^T$ is the sound attenuation through the sample in the measuring cell when the sample is at T. $d\alpha/dT$ is the sound attenuation slope as a function of temperature; C is the electrical conductivity; and constants $K_1$–$K_5$, $K_6$–$K_{10}$, $K_{11}$–$K_{15}$, $K_{16}$–$K_{20}$ and $K_{21}$–$K_{25}$ are derived by empirical correlation with actual, separate analyses performed by known chemical methods. The set of five equations above is referred to herein as "data processing means". Obviously, if N components have to be determined, N independent physical parameters need to be measured simultaneously. Thus, for 4 components (see Example below), the measurement of four parameters will suffice.

EXAMPLE

On-line Determination of %F and Percentages of SNF Components in Milk

The content of a milk sample taken from cow was determined on-line using the following procedure: The ultrasonic device was connected to the milking system. A milk sample was transmitted to the test cell using a piston. The milk sample was brought to 20° C. and 30° C. For each temperature ultrasound attenuation, ultrasound velocity, their temperature derivatives, as well as electrical conductivity were measured. The electronic signals were transmitted to a data processing unit, and the main milk components were computed. The milk components were also analyzed by IR-Fosselectric method (Foss Milko-scan-Milkotester MK III) and the results obtained by the two methods were compared. The results are summarized in Table I.

Table I: Milk sample analysis: comparison between the results obtained by the method of the present invention (NDT) and by the IR-Fosselectric method ("Ref"). Components analyzed: Fat, Protein, Lactose and Somatic Cells.

TABLE I

Milk sample analysis: comparison between the results obtained by the method of the present invention (NDT) and by the IR-Fosselectric method ("Ref"). Components analyzed: Fat, Protein, Lactose and Somatic Cells.

| Fat (NDT) | Fat (Ref) | differ (%) | Protein (NDT) | Protein (Ref) | differ (%) | Lactose (NDT) | Lactose (Ref) | differ (%) | Somatic Cells (NDT) | Somatic cells (Ref) |
|---|---|---|---|---|---|---|---|---|---|---|
| 3.82 | 3.85 | 0.78 | 3.27 | 3.23 | 1.24 | 4.8 | 4.66 | 3.00 | 159 | 108 |
| 4.53 | 4.62 | 1.95 | 4.11 | 4.13 | 0.48 | 4.99 | 5.16 | 3.29 | 111 | 94 |
| 3.08 | 2.97 | 3.70 | 2.78 | 2.8 | 0.71 | 4.84 | 4.69 | 3.20 | 39 | 17 |
| 2.89 | 2.95 | 2.03 | 3.44 | 3.49 | 1.43 | 5 | 4.94 | 1.21 | 86 | 44 |
| 2.99 | 2.95 | 1.36 | 3.44 | 3.5 | 1.71 | 5.07 | 4.94 | 2.63 | 68 | 44 |
| 4.5 | 4.66 | 3.43 | 3.53 | 3.6 | 1.94 | 4.85 | 5 | 3.00 | 143 | 62 |
| 3.25 | 3.36 | 3.27 | 3.15 | 3.19 | 1.25 | 4.88 | 4.91 | 0.61 | 116 | 87 |
| 3.84 | 3.75 | 2.40 | 2.97 | 2.95 | 0.68 | 4.85 | 4.69 | 3.41 | 125 | 91 |
| 4.27 | 4.4 | 2.95 | 3.5 | 3.6 | 2.78 | 4.87 | 4.97 | 2.01 | 130 | 127 |
| 4.21 | 4.32 | 2.55 | 3.34 | 3.44 | 2.91 | 4.83 | 5 | 3.40 | 146 | 60 |
| 4.84 | 4.81 | 0.62 | 3.46 | 3.55 | 2.54 | 4.9 | 4.88 | 0.41 | 120 | 372 |
| 3.74 | 3.82 | 2.09 | 2.95 | 3.02 | 2.32 | 4.91 | 5.04 | 2.58 | 99 | 48 |
| 3.29 | 3.29 | 0.00 | 3.56 | 3.57 | 0.28 | 5.05 | 4.9 | 3.06 | 75 | 145 |
| 4.2 | 4.18 | 0.48 | 3.53 | 3.56 | 0.84 | 4.84 | 4.71 | 2.76 | 148 | 127 |

TABLE I-continued

Milk sample analysis: comparison between the results obtained
by the method of the present invention (NDT) and by the IR-Fosselectric
method ("Ref"). Components analyzed: Fat, Protein, Lactose and Somatic Cells.

| Fat (NDT) | Fat (Ref) | differ (%) | Protein (NDT) | Protein (Ref) | differ (%) | Lactose (NDT) | Lactose (Ref) | differ (%) | Somatic Cells (NDT) | Somatic cells (Ref) |
|---|---|---|---|---|---|---|---|---|---|---|
| 3.03 | 3.08 | 1.62 | 3.07 | 3.17 | 3.15 | 5 | 5.02 | 0.40 | 78 | 411 |
| 4.1 | 4.18 | 1.91 | 3.63 | 3.68 | 1.36 | 4.88 | 4.83 | 1.04 | 133 | 175 |
| 3.04 | 2.98 | 2.01 | 2.99 | 2.91 | 2.75 | 4.59 | 4.52 | 1.55 | 710 | 1052 |
| 4.64 | 4.7 | 1.28 | 3.03 | 3.11 | 2.57 | 4.71 | 4.81 | 2.08 | 101 | 71 |
| 5.37 | 5.41 | 0.74 | 3.47 | 3.41 | 1.76 | 4.74 | 4.67 | 1.50 | 203 | 242 |
| 3.89 | 3.87 | 0.52 | 2.92 | 3.01 | 2.99 | 4.81 | 4.98 | 3.41 | 139 | 112 |
| 5.22 | 5.33 | 2.06 | 2.8 | 2.73 | 2.56 | 4.35 | 4.29 | 1.40 | 330 | 946 |
| R | 0.996 | | | 0.986 | | | 0.894 | | | 0.847 |
| STD DEV | | 1.041 | | | 0.913 | | | 1.053 | | |

The comparison shows that the results obtained with the method and apparatus of the present invention are accurate, and very close to results obtained with accepted chemical methods.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. A method of analyzing a fluid, comprising the steps of:
   a) bringing a sample of the fluid to a plurality of successive temperatures;
   b) measuring N physical parameters of said sample, N being at least three, at each said temperature, wherein said physical parameters include at least two acoustical parameters and at least one electrical parameter; and
   c) determining simultaneously the concentrations of N components of the fluid, N being at least three, using said physical parameters, thereby obtaining a quantitative composition of the fluid.

2. The method of claim 1, wherein said at least one electrical parameter is electrical conductivity.

3. The method of claim 1, wherein said at least one acoustical parameter is selected from the group consisting from sound velocity and sound attenuation, and wherein said measuring of said at least one acoustic parameter is effected by steps including generating an acoustic field in the sample.

4. The method of claim 1, wherein said electrical conductivity is determined from the active component of the complex electric impedance of said sample.

5. The method of claim 3, wherein said acoustical field is a cylindrical standing wave field.

6. The method of claim 1, wherein said bringing to a plurality of successive temperatures is effected in a stepwise fashion.

7. The method of claim 1, wherein said bringing to a plurality of successive temperatures is effected through continuous temperature scanning.

8. The method of claim 1, wherein said determining includes simultaneously solving a system of N equations, N being at least three, based on said at least two acoustical parameters and at least one electrical parameter at said plurality of successive temperatures.

9. The method of claim 1, wherein said fluid is milk, and wherein said N components are selected from the group consisting from butterfat, protein, lactose, mineral salts and water.

10. The method of claim 1, further comprising:
    d) providing a reference fluid sample;
    e) bringing said reference sample to the same said plurality of successive temperatures;
    f) measuring in said reference sample the same said N physical parameters;
    e) using said measurements in said reference sample to aid in said determining.

11. The method of claim 10, wherein said determining includes simultaneously solving a system of N linear equations based on said N physical parameters obtained at said plurality of successive temperatures.

12. The method of claim 10, wherein said fluid is milk, and wherein said N components are selected from the group consisting from butterfat, protein, lactose, mineral salts and water.

13. An apparatus for the simultaneous determination of the concentrations of N components of a fluid, N being at least three, comprising:
    a) a measuring unit including at least one acoustical and at least one electrical measurement cells;
    b) means for introducing a sample of the fluid into said measuring unit.
    c) thermostating means to bring said fluid sample to a series of temperatures;
    d) means for measuring acoustical and electrical parameters of said fluid sample; and
    e) data processing means for evaluating the concentrations of the N components from said measured acoustical and electrical parameters.

14. The apparatus of claim 13, wherein said measuring acoustical and electrical cells are placed in series forming a single tube.

15. The apparatus of claim 13, wherein said acoustical cell is a standing wave resonator.

16. The apparatus of claim 13, wherein said acoustical cell includes a metal tube with two piezotransducers.

17. The apparatus of claim 16, wherein said thermostating means include a thermosensor, a thermal jacket, a Peltier element, and a heat sink.

18. The apparatus of claim 16, wherein said metal tube of acoustical cell serves as an electrode for said electrical cell, and wherein a second circular electrode of said electrical cell is separated from said metal tube of said acoustical cell by a segment of non-conductive tube.

19. The apparatus of claim 13, wherein said at least one acoustical cell includes a first and a second symmetrically placed acoustical cells, and wherein said second acoustical cell is filled with a reference fluid.

20. The apparatus of claim 19, wherein said second acoustical cell is sealed with an elastic plug.

* * * * *